United States Patent [19]

Seed

[11] Patent Number: 4,895,845
[45] Date of Patent: Jan. 23, 1990

[54] METHOD OF ASSISTING WEIGHT LOSS

[76] Inventor: John C. Seed, 763 Kingston Rd., Princeton, N.J. 08540

[21] Appl. No.: 907,837

[22] Filed: Sep. 15, 1986

[51] Int. Cl.4 .................. A61K 31/50; A61K 31/495; A61K 31/44; A61K 31/135
[52] U.S. Cl. .................................... 514/252; 514/280; 514/649; 514/651; 514/910
[58] Field of Search ............... 514/280, 910, 252, 649, 514/651

[56] References Cited

U.S. PATENT DOCUMENTS

| | | | |
|---|---|---|---|
| 4,310,524 | 1/1982 | Wiech et al. | 514/280 |
| 4,442,113 | 4/1984 | Lassen et al. | 424/267 |
| 4,525,359 | 6/1985 | Greenway et al. | 514/280 |
| 4,626,549 | 12/1986 | Molloy et al. | 514/651 |

FOREIGN PATENT DOCUMENTS

2048926  4/1972  Fed. Rep. of Germany ...... 514/280

OTHER PUBLICATIONS

Science, 198:1178–1180—Wurtman et al.
Chem. Abst. 88:130914d—Reinhard et al.
The Merck Index—9th—1976—Items #396, and 3902.
Goodman & Gilman—The Pharmacological Basis of Therapeutics, 6th Ed.—p. 172.

*Primary Examiner*—Douglas W. Robinson
*Assistant Examiner*—Raymond J. Henley, III
*Attorney, Agent, or Firm*—Richard C. Woodbridge

[57] ABSTRACT

A method of assisting weight loss involving the combined administration of a rauwolfia alkaloid and at least one antidepressant, selected from the groups consisting of aminoazoles, phenoxyphenylpropylamines, and aminopropiophenones, in a daily regimen with the optional co-administration of one or more sympathomimetic anorexic agents. In a typical embodiment of this method, reserpine and trazodone are administered in a daily regimen with diethylpropion, fenfluramine or both diethylpropion and fenfluramine.

10 Claims, No Drawings

METHOD OF ASSISTING WEIGHT LOSS

BACKGROUND OF THE INVENTION

The present invention pertains to a method of assisting weight loss in patients which involves the administration of a unique combination of pharmaceutically active ingredients to suppress appetite and to a method of maintaining that weight loss by long term, chronic administration of all or a portion of the components of this unique combination.

While the causes of excess body weight and obesity are complex, a common denominator in the overweight person's diet is a caloric intake which exceeds his body's expenditure. A methodology which combines dietary restriction with increased physical activity will maximize potential weight loss. However, the obese patient has typically developed eating and activity patterns which are counterproductive to achieving weight reduction. One efficacious treatment of obesity utilizes appetite suppressive drugs as adjuncts in a weight reduction program. Thus increased compliance with and tolerance to a low-calorie diet will often develop when an anorexic drug is prescribed for the well-motivated patient. In many instances, however, the use of an anorexic agent may produce undesired side effects or its effect may diminish over a period of time.

DETAILED DESCRIPTION

The present invention pertains to a method of assisting weight loss in patients through the administration of a unique combination of pharmaceutically active ingredients to suppress appetite. In particular, the present invention involves the concomitant administration of effective amounts of a rauwolfia alkaloid and at least one antidepressant selected from the group consisting of aminoazoles, phenoxyphenylpropylamines, and aminopropiophenones in a single or multiple daily dose during a weight loss regimen. While the mechanism of interaction between the rauwolfia alkaloid and the selected antidepressants is not fully understood, the effectiveness of this method of assisting weight loss has been demonstrated in a number of clinical studies, discussed more fully herein.

Rauwolfia alkaloids have been used as antihypertensive therapeutic agents in the management of elevated blood pressure. Infrequently, rauwolfia alkaloid derivatives have been prescribed in the management of agitated psychotic states, such as schizophrenia.

Typical of the known rauwolfia alkaloids are deserpidine, alperaxylon, reserpine, and rauwolfia serpentina. Of these, reserpine is preferred for the present method because of its availability and established clinical history. Oral dosage of the rauwolfia alkaloid should be carefully adjusted according to individual tolerance and response, using the lowest possible effective dosage. Typically, the amount of rauwolfia alkaloid administered daily is from about 0.001 to about 0.01 mg per kg of body weight.

The aminoazole antidepressants, such as etoperidone, mepiprazole, and trazodone, are chemically unrelated to other currently available antidepressants; see; e.g., U.S. Pat. Nos. 3,857,845; 3,491,097; and 3,381,009. Aminoazole antidepressants are therapeutically indicated for the relief of major depression and some clinical studies have indicated the aminoazole antidepressants may be of value in the treatment of schizophrenic disorders or alcohol dependency. While the aminoazole advantageously provides an antidepressant effect, it appears to also assist directly in weight loss and thus is distinguished from other antidepressants such as the tricyclics.

Of the aminoazole antidepressants, trazodone is preferred because of its availability. As a clinically co-active anorexic agent, trazodone is administered in a daily amount of from about 0.1 to 6.0 mg per kg of body weight. The effective dosage for each individual is adjusted on the basis of clinical response.

Typically, a combined dosage of from about 0.001 to 0.01 mg per kg of body weight of reserpine and 0.1 to 6.0 mg per kg of body weight of trazodone is administered daily. Conveniently, the two can be administered at the same time.

The preferred phenoxyphenylpropylamine antidepressant is fluoxetine. Clinical studies indicate fluoxetine relieves the symptoms of major depressive illness. In contrast to the tricyclic antidepressants, fluoxetine does not inhibit the noradrenergic uptake system. This phenoxyphenylpropylamine antidepressant should be administered within the range of from about 0.1 to 1.5 mg per kg body. However, the effective dosage should be adjusted on the basis of individual clinical responses.

The aminopropiophenone antidepressants are therapeutically indicated for relief of depression in patients who are unresponsive or intolerant of other available antidepressants. Bupropion, the preferred aminopropiophenone antidepressant, is not chemically related to other antidepressants, but is pharmacologically similar to the tricyclic compounds; see; e.g., U.S. Pat. Nos. 3,819,706 and 3,885,046. As an effectic anorexic agent, bupropion is typically administered in a daily amount of from about 0.05 to about 7.0 mg per kg of body weight.

As the duration of action for these pharmaceutically active agents typically exceeds 24 hours, the frequency of administration need not be bound to a daily dosage schedule. An administration regimen sufficient to supply effective daily dosages may be satisfied by single daily doses, multiple daily doses, alternate day doses, multiple weekly doses, or weekly doses.

Since the rate of weight loss will vary from patient to patient, and is not consistent for each patient, the effectiveness of the treatment is best observed over a period of weeks. The patient should be carefully monitored with regard to other medications and to overall physical condition. Exercise naturally assists the treatment.

In the combined administration of the rauwolfia alkaloid and one or more of the specified antidepressants, the administration of one or more of the sympathomimetic anorexic agents has proved successful in some instances in promoting patient compliance to a calorically-restricted diet. In this embodiment the sympathomimetic anorexic agents are administered in an effective amount, normally its recommended dosage, over a portion of the time during which the rauwolfia alkaloid and one or more of the specified antidepressants are being administered.

The term sympathomimetic anorexic agents refers to compounds pharmacologically similar to amphetamine, dextroamphetamine, methamphetamine, benzphetamine, phentermine, chlorphentermine, fenfluramine, dextrofenfluramine, clortermine, mephentermine, phenmetrazine, phendimetrazine, diethylpropion, mazindol, phenylpropanolamine, ephedrine, pseudoephedrine and methylphenidate.

A representative sympathomimetic anorexic agent is diethylpropion. The usual adult dosage of diethylpropion is typically from about 0.15 to about 4.0 mg per kg of body weight but again the dosage should be individualized to obtain the most desirable effect. Diethylpropion is a known stimulant of the central nervous system and this medication generally is administered early in the normal waking hours of the patient to prevent possible insomnia. Surprisingly, however, the stimulating effects of diethylpropion are partially surpressed in many patients in the practice of the present invention so that, in such cases, it can be administered later in the day.

Alternatively, the sympathomimetic anorexic can be fenfluramine. This can be administered in the aforementioned regimen of the rauwolfia alkaloid and one or more of the specified antidepressants as a useful adjunct to weight reduction. The preferred dosage of fenfluramine is typically from about 0.2 to about 1.8 mg per kg of body weight but should be individualized to obtain the most therapeutic response at the lowest effective dose. Fenfluramine and dextrofenfluramine are pharmacologically distinct from other sympathomimetic anorexics in that their mode of action results in the depression of the central nervous system. Thus, fenfluramine and dextrofenfluramine can be administered later in the day than is the case with many other sympathomimetic agents. This differentiating characteristic of fenfluramine and dextrofenfluramine also can be utilized to permit co-administration of these anorexic agents with other sympathomimetic compounds, such as diethylpropion, without exacerbating potential side effects, such as insomnia, restlessness, or irritability.

An alternate embodiment of weight loss involves the co-administration of at least one or more of the specified antidepressants with one or more sympathomimetic anorexic agents. While the appetite suppressant drugs are known to be useful adjuncts to a weight loss program, the usual duration of their efficacy is brief. After about six to twelve weeks of administration, tolerance to some of the sympathomimetic anorexic agents develops and they are no longer dependable aids in controlling appetite. Significant increases in the efficacy of appetite suppression drugs is observed in a method which utilizes at least one antidepressant selected from the groups consisting of aminoazoles, phenoxyphenylpropylamines and aminopropiophenones, during the co-administration of sympathomimetic anorexic agents. Clinical studies thus demonstrate potentiation in the duration of action of the sympathomimetic anorexics, such as diethylpropion and fenfluramine, when administered in a daily regimen with at least one or more of the specified antidepressants.

The preferred dosage of the antidepressant trazodone in this embodiment is from about 0.1 to 6.0 mg per kg of body weight during the co-administration of the sympathomimetic anorexic agent. In this embodiment, diethylpropion is administered at a dosage of about 0.15 to about 4.0 mg per kg of body weight whereas fenfluramine is administered in a regimen with the selected antidepressant in the range of from about 0.2 to about 1.8 mg per kg of body weight. The most effective dosages for the combined administration of the diethylpropion and the fenfluramine during the co-administration of one or more of the specified antidepressants should be within the ranges previously recited. However, the preferred dosages should be adjusted on the basis of the individual clinical response of each patient.

The following examples typify the mode of application for the method of assisting weight loss.

EXAMPLE 1

Patient A, a 61 year old male, was diagnosed as both hypertensive and diabetic. He was observed to be 23 lbs. over his ideal weight of 185 lbs. The combined administration of reserpine and trazodone during a 40 week regimen resulted in a weight loss of 17.2 lbs. Subsequently, fenfluramine and then both fenfluramine and diethylpropion were administered in conjunction with the reserpine and trazodone as adjuncts to weight reduction. The following table enumerates the dosage and weight changes observed during the 75 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | 100 | — | — | 1 | +5.5 |
| .25 | 200 | — | — | 8 | −7.0 |
| .50 | 200 | — | — | 31 | −15.7 |
| .50 | 200 | 20 | — | 4 | −1.3 |
| .50 | 200 | 40 | — | 8 | −1.0 |
| .50 | 200 | 60 | — | 5 | +2.7 |
| .50 | 200 | 60 | 75 | 9 | −1.2 |
| .50 | 200 | 80 | 75 | 9 | −2.0 |

EXAMPLE 2

Patient B, a 56 year old female, was diagnosed as hypertensive. She was observed to be 75 lbs. over her ideal weight of 117 lbs. The combined administration of reserpine and trazodone during a 62 week regimen resulted in a weight loss of 26.5 lbs. The following table enumerates the dosage and weight changes observed during the 120 week therapy.

| Daily Dosages (mg) | | Period of Treatment (weeks) | Weight Change (lbs.) |
|---|---|---|---|
| Reserpine | Trazodone | | |
| .25 | 0 | 7 | +1.0 |
| .25 | 150 | 39 | −21.0 |
| .25 | 200 | 23 | −5.5 |
| .25 | — | 46 | +12.2 |
| .25 | 150 | 5 | −3.2 |

EXAMPLE 3

Patient C, a 60 year old male, was diagnosed as hypertensive. He was observed to be 38 lbs. over his ideal weight of 165 lbs. The combined administration of reserpine and trazodone during a 41 week regimen resulted in a weight loss of 25.3 lbs. The following table enumerates the dosage and weight changes observed during the 41 week therapy.

| Daily Dosages (mg) | | Period of Treatment (weeks) | Weight Change (lbs.) |
|---|---|---|---|
| Reserpine | Trazodone | | |
| .25 | 100 | 2 | +7.5 |
| .25 | 200 | 35 | −32.8 |

EXAMPLE 4

Patient D, a 62 year old male, was diagnosed as hypertensive. He was observed to be 62 lbs. over his ideal weight of 158 lbs. The combined administration of reserpine and trazodone during a 26 week regimen resulted in a weight loss of 16 lbs. Subsequently, diethylpropion and then both diethylpropion and fenfluramine were administered in conjunction with the reserpine and trazodone as adjuncts to weight reduction. The following table enumerates the dosage and weight changes observed during the 68 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | 200 | — | — | 1 | +0.8 |
| .50 | 200 | — | — | 16 | −12.0 |
| .50 | 300 | — | — | 5 | −2.0 |
| —[a] | 300 | — | — | 3 | −0.5 |
| .50 | 300 | — | — | 1 | −1.5 |
| .50 | 300 | — | 75 | 1 | +1.0 |
| .50 | 300 | — | — | 6 | +4.5 |
| .50 | 300 | — | 75 | 2 | −3.7 |
| .50 | 300 | 20 | 75 | 2 | −3.3 |
| .50 | 300 | — | 75 | 2 | −0.7 |
| .50 | 300 | 40 | — | 3 | −0.8 |
| .50 | 300 | — | 75 | 2 | +3.5 |
| .50 | 300 | 20 | 75 | 4 | −2.5 |
| .50 | 300 | 40 | 75 | 4 | −4.8 |
| .50 | 300 | — | — | 1 | −0.2 |
| .75 | 300 | — | — | 3 | +0.5 |
| .75 | 300 | 40[b] | 75[b] | 5 | +6.5 |
| .75 | 300 | 20 | 75 | 3 | −2.8 |
| .75 | 300 | 40 | 75 | 2 | −2.7 |
| .75 | 300 | 80 | 75 | 2 | −3.0 |

[a]Patient omission.
[b]Patient varied administration to alternate weeks.

EXAMPLE 5

Patient E, a 73 year old female, was diagnosed as hypertensive. She was observed to be 10 lbs. over her ideal weight of 127 lbs. The combined administration of reserpine and trazodone during a 25 week regimen resulted in a weight gain of 2 lbs. Subsequently, diethylpropion was administered in conjunction with the reserpine and trazodone as an adjunct to weight reduction. The following table enumerates the dosage and weight changes observed during the 68 week therapy.

| Daily Dosages (mg) | | | Period of Treatment (weeks) | Weight Change (lbs.) |
|---|---|---|---|---|
| Reserpine | Trazodone | Diethylpropion | | |
| .10 | 0 | — | 4 | +2.0 |
| .10 | 200 | — | 4 | −2.3 |
| .10 | — | — | 4 | +4.0 |
| .10 | 150 | — | 4 | −1.2 |
| .25 | 150 | — | 8 | +4.0 |
| .50 | 150 | — | 3 | +1.2 |
| .50 | 200 | — | 8 | −0.7 |
| .50 | 200 | 75 | 6 | −11.0 |
| .50 | 200 | — | 2 | +3.5 |
| .50 | 200 | 75 | 10 | −8.8 |
| .50 | 200 | — | 11 | −4.4 |
| .25 | 100 | — | 6 | 0.0 |

EXAMPLE 6

Patient F, a 23 year old male, was diagnosed as obese. He was observed to be 55 lbs. over his ideal weight of 190 lbs. Diethylpropion administration was in conjunction with the reserpine and trazodone and resulted in a weight loss of 45 lbs. during the 30 week regimen. The following table enumerates the dosage and weight changes observed during the 31 week therapy.

| Daily Dosages (mg) | | | Period of Treatment (weeks) | Weight Change (lbs.) |
|---|---|---|---|---|
| Reserpine | Trazodone | Diethylpropion | | |
| .25 | 50 | — | 1 | +0.3 |
| .25 | 50 | 75 | 7 | −15.8 |
| .25 | 100 | 75 | 3 | +3.2 |
| .25 | 100 | 25[a] | 5 | −10.4 |
| .25 | 150 | 25 | 5 | −6.0 |
| .12 | 200 | 25 | 2 | −5.3 |
| .12 | 200 | 75[a] | 2 | −7.5 |
| .12 | 200 | 75 | 6 | −3.0 |

[a]Alternate day administration.

EXAMPLE 7

Patient G, a 45 year old female, was diagnosed as hypertensive. She was observed to be 84 lbs. over her ideal weight of 145 lbs. The combined administration of reserpine and trazodone was augmented with both diethylpropion and fenfluramine during a five week regimen which resulted in a weight loss of 14.6 lbs. The following table enumerates the dosage and weight changes observed during the 26 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| — | — | — | 75 | 2 | +1.5 |
| .25 | 50 | — | 75 | 1 | −3.0 |
| .25 | 100 | — | 75 | 1 | −0.2 |
| .25 | 300 | — | 75 | 1 | +2.6 |
| .50[a] | 300[a] | 20 | 75 | 5 | −14.6 |
| — | — | 20 | 75 | 16 | −20.2 |

[a]Patient reported drowsiness; discontinued reserpine and trazodone.

EXAMPLE 8

Patient H, a 64 year old female, was diagnosed as both neuropathic and obese. She was observed to be 60 lbs. over her ideal weight of 140 lbs. Patient reported intolerance to either diethylpropion or fenfluramine when administered in conjunction with the reserpine and trazodone. The following table enumerates the dosage and weight changes observed during the 46 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | 400 | — | — | 4 | +1.3 |
| .25 | 400 | — | 75 | 1 | −3.7 |
| .25 | 400 | — | — | 2 | −3.3 |
| .25 | 400 | — | 75 | 2 | +0.7 |
| .25 | 100 | — | — | 1 | +2.8 |
| .25 | 100 | — | 75 | 1 | −2.8 |
| .25 | 100 | — | — | 1 | +3.0 |
| — | 200 | — | — | 16 | +2.3 |
| — | — | — | — | 12 | −2.7 |
| — | — | 20 | — | 2 | +3.0 |
| — | — | — | 75 | 2 | −6.3 |
| — | — | — | 25 | 2 | +3.5 |

EXAMPLE 9

Patient I, a 68 year old male, was diagnosed as both diabetic and obese. He was observed to be 200 lbs. over his ideal weight of 120 lbs. The combined administration of reserpine and trazodone during a 7 week regimen resulted in a weight loss of 9 lbs. The following table enumerates the dosage and weight changes observed during the 15 week therapy.

| Daily Dosages (mg) | | Period of Treatment (weeks) | Weight Change (lbs.) |
|---|---|---|---|
| Reserpine | Trazodone | | |
| .25 | — | 8 | +4.5 |
| .25 | 200 | 2 | −1.5 |
| .50 | 200 | 5 | −7.8 |

EXAMPLE 10

Patient J, a 62 year old male, was diagnosed as both hypertensive and diabetic. He was observed to be 50 lbs. over his ideal weight of 160 lbs. The combined administration of reserpine and trazodone in conjunction with fenfluramine resulted in a weight loss of 30 lbs. during a 25 week regimen. The following table enumerates the dosage and weight changes observed during the 28 week therapy.

| Daily Dosages (mg) | | | Period of Treatment (weeks) | Weight Change (lbs.) |
|---|---|---|---|---|
| Reserpine | Trazodone | Fenfluramine | | |
| — | — | — | 1 | 0.0 |
| — | — | 40 | 1 | +3.0 |
| .25 | 50 | 40 | 26 | −30.5 |

EXAMPLE 11

Patient K, a 30 year old female, was diagnosed as obese. She was observed to be 54 lbs. over her ideal weight of 127 lbs. The combined administration of reserpine and trazodone was augmented by fenfluramine as an adjunct to weight reduction. During this 12 week regimen, a weight loss of 7 lbs. was recorded. The following table enumerates the dosage and weight changes observed during the 20 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | — | — | — | 2 | +0.8 |
| .25 | 50 | — | — | 1 | −3.4 |
| .25 | 50 | — | 25 | 2 | +0.7 |
| .25 | 50 | 20 | — | 1 | −1.0 |
| .25 | 50 | 40 | — | 1 | −1.0 |
| .25 | 100 | 40 | — | 1 | −1.0 |
| .50 | 100 | 40 | — | 2 | −1.7 |
| .50 | 100 | 60 | — | 3 | −1.3 |
| .50 | 100 | 40 | — | 4 | −1.0 |
| — | — | — | — | 3[a] | +1.3 |

[a]Patient pregnant; discontinued medication.

EXAMPLE 12

Patient L, a 39 year old male, was diagnosed as hypertensive. He was observed to be 76 lbs. over his ideal weight of 166 lbs. The combined administration of reserpine and trazodone was augmented by fenfluramine and then both fenfluramine and diethylpropion as adjuncts to weight reduction. During a 13 week regimen this combination of pharmaceutically-active agents resulted in a weight loss of 29 lbs. The following table enumerates the dosage and weight changes observed during the 26 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | 50 | — | — | 1 | +5.3 |
| .25 | 100 | — | — | 1 | +0.7 |
| .25 | 100 | 20 | — | 2 | +0.6 |
| .25 | 100 | 40 | — | 2 | +1.4 |
| .50 | 100 | 80 | — | 2 | −1.7 |
| — | 100 | 80 | 75 | 4 | −2.7 |
| — | 200 | 80 | 75 | 1 | −5.3 |
| .25 | 200 | 80 | 75 | 13 | −29.0 |

EXAMPLE 13

Patient M, a 35 year old male, was diagnosed as obese. He was observed to be 47 lbs. over his ideal weight of 140/lbs. The combined therapy of reserpine and trazodone was augmented with diethylpropion and then both diethylpropion and fenfluramine as adjuncts to weight reduction. The following table enumerates the dosage and weight changes observed during the 20 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| — | 50 | — | 75 | 1 | +1.6 |
| .25 | 50 | — | 75 | 2 | −3.2 |
| .50 | 50 | 20 | 75 | 2 | −0.2 |
| .50 | 50 | 40 | 75 | 2 | −2.3 |
| .50 | 50 | 20 | 75 | 3 | +0.3 |
| .50 | 50 | 40 | 75 | 4 | −0.8 |
| .25 | 50 | 60 | 100 | 6 | +1.8 |

EXAMPLE 14

Patient N, a 60 year old female, was diagnosed as obese. She was observed to be 110 lbs. over her ideal weight of 135 lbs. The administration of reserpine was augmented with diethylpropion and then both diethylpropion and fenfluramine as adjuncts to weight reduction. When this regimen was supplemented with trazodone for 17 weeks, a weight loss of 15 lbs. was recorded. The following table enumerates the dosage and weight changes observed during the 21 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | — | — | 75 | 1 | −1.6 |
| .25 | — | 20 | 75 | 1 | +1.6 |
| .50 | — | 40 | 75 | 1 | −2.0 |
| .50 | — | 20 | 75 | 1 | −0.6 |
| .50 | 50 | 20 | 75 | 1 | +2.8 |
| .50 | 50 | 60 | 75 | 1 | −2.5 |
| .50 | 50 | 40 | 75 | 1 | −2.3 |
| .50 | 100 | 40 | 75 | 3 | −2.4 |
| .50 | 50 | 40 | 75 | 1 | 0.0 |
| .50 | 50 | 80 | 75 | 3 | −1.6 |
| .50 | 50 | — | 75 | 1 | −0.2 |
| .50 | 50 | 80 | 75 | 1 | −1.5 |
| .50 | 100 | 80 | 75 | 2 | −0.3 |
| .50 | 100 | 90 | 100 | 1 | −2.0 |
| .50 | 100 | 80 | 100 | 1 | −2.0 |
| .50 | 125 | 80 | 100 | 1 | −0.2 |

EXAMPLE 15

Patient O, a 40 year old male, was diagnosed as obese. He was observed to be 60 lbs. over his ideal weight of 186 lbs. The combined administration of reserpine and trazodone was augmented with diethylpropion and then both diethylpropion and fenfluramine. The following table enumerates the dosage and weight changes observed during the 13 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | — | — | 75 | 1 | −3.2 |
| .25 | 50 | — | 75 | 1 | 0.0 |
| .25 | 50 | — | 100 | 1[a] | +4.0 |
| .25 | 50 | — | 100 | 4 | −7.0 |
| .25 | 50 | 20 | 100 | 1 | −1.5 |
| .25 | — | 20 | 100 | 5 | −6.7 |

[a]Patient took medication intermittently

EXAMPLE 16

Patient P, a 60 year old female, was diagnosed as diabetic. She was observed to be 63 lbs. over her ideal weight of 120 lbs. The combined administration of reserpine and trazodone during a 7 week regimen resulted in no net weight loss. Subsequently, diethylpropion and then both diethylpropion and fenfluramine were administered in conjunction with reserpine as adjuncts to weight reduction. The following table enumerates the dosage and weight changes observed during the 65 week therapy.

| Daily Dosages (mg) | | | | Period of Treatment (weeks) | Weight Change (lbs.) |
|---|---|---|---|---|---|
| Reserpine | Trazodone | Fenfluramine | Diethylpropion | | |
| .25 | 200 | — | — | 2 | −0.6 |
| .25 | 100 | — | — | 2 | −0.2 |
| .25 | 50 | — | — | 3 | +1.0 |
| .25 | — | — | 100[a] | 9 | −1.2 |
| .25 | — | — | 50 | 7 | −0.6 |
| .25 | — | 40 | — | 1 | +0.3 |
| .25 | — | — | — | 18 | +3.3 |
| .25 | — | 40 | 37.5 | 6 | −5.6 |
| .25 | — | — | — | 18 | +6.2 |

[a]Patient experienced insomnia on this dosage.

EXAMPLE 17

Patient Q, a 65 year old female, was diagnosed as hypertensive. She was observed to be 30 lbs. over her ideal weight of 132 lbs. The combined administration of reserpine and trazodone was augmented with fenfluramine for three weeks during which time the patient reported a variety of side effects. The following table enumerates the dosage and weight changes observed during the 7 week therapy.

| Daily Dosages (mg) | | | Period of Treatment (weeks) | Weight Change (lbs.) |
|---|---|---|---|---|
| Reserpine | Trazodone | Fenfluramine | | |
| .25 | 50 | — | 2 | +2.5 |
| .25 | 50 | 20 | 3 | −1.7 |
| .25 | 50 | — | 2 | −3.6 |

EXAMPLE 18

Patient R, a 36 year old male, was diagnosed as hypertensive. He was observed to be 83 lbs. over his ideal weight of 161 lbs. During a 22 week regimen of trazodone, diethylpropion and fenfluramine, a weight loss of 24.3 lbs. was recorded. The following table enumerates the dosage and weight changes observed during the 28 week therapy.

| Daily Dosages (mg) | | | Period of Treatment (weeks) | Weight Change (lbs.) |
|---|---|---|---|---|
| Trazodone | Fenfluramine | Diethylpropion | | |
| 100 | — | — | 1 | −3.7 |
| 100 | — | 75 | 5 | +1.0 |
| 100 | 20 | 75 | 7 | −11.0 |
| 100 | 40 | 75 | 9 | −5.8 |
| 100 | 80 | 75 | 6 | −4.8 |

EXAMPLE 19

Patient S, a 52 year old female, was diagnosed as hypertensive. She was observed to be 12 lbs. over her ideal weight of 115 lbs. The following table enumerates the dosage and weight changes observed during the 13 week therapy.

| Daily Dosages (mg) | | | Period of Treatment (weeks) | Weight Change (lbs.) |
|---|---|---|---|---|
| Reserpine | Trazodone | Fenfluramine | | |
| — | 200 | — | 3 | +1.0 |
| — | 200 | 20 | 2 | −2.8 |
| — | 200 | 40 | 2 | +2.6 |
| — | 200 | 60 | 2 | −1.0 |
| .25 | 200 | 40 | 2 | −2.6 |
| .25 | 200 | 60 | 2 | −1.2 |

EXAMPLE 20

Patient T, a 29 year old male, was diagnosed as hypertensive. He was observed to be 36 lbs. over his ideal weight of 155 lbs. The following table enumerates the dosage and weight changes observed during the 26 week therapy.

| Daily Dosages (mg) | | | Period of Treatment (weeks) | Weight Change (lbs.) |
|---|---|---|---|---|
| Trazodone | Fenfluramine | Diethylpropion | | |
| 200 | — | 75 | 5 | 0.0 |
| 200 | 20 | 75 | 2 | −1.7 |
| 200 | — | 75 | 19 | −3.7 |

What is claimed is:

1. A method of assisting weight loss in a human in need thereof which comprises administering to said human, over a sustained period of time, both a rauwolfia alkaloid in the form of reserpine, and at least one antidepressant selected from the group consisting of trazodone, bupropion and fluoxetine in an administration regimen sufficient to supply effective daily dosages thereof for assisting weight loss.

2. The method of claim 1 wherein said antidepressant is trazodone and both reserpine and trazodone are administered concomitantly.

3. The method of claim 1 wherein the daily dosage of reserpine is between about 0.001 and about 0.01 milligram per kilogram of human body weight.

4. The method of claim 1 wherein said antidepressant is trazodone and the daily dosage of trazodone is between about 0.1 and about 6.0 milligram per kilogram of human body weight.

5. The method of claim 1 wherein said antidepressant is fluoxetine and both reserpine and fluoxetine are administered concomitantly.

6. The method of claim 1 wherein the daily dosage of reserpine is between about 0.001 and about 0.01 milligram per kilogram of human body weight.

7. The method of claim 1 wherein said antidepressant is fluoxetine and the daily dosage of fluoxetine is between about 0.1 and about 1.5 milligram per kilogram of human body weight.

8. The method of claim 1 wherein the rauwolfia alkaloid is reserpine, and both trazodone and fluoxetine are administered, said reserpine, trazodone, and fluoxetine being administered in a regimen sufficient to supply effective daily dosages thereof for assisting weight loss.

9. The method of claim 1 wherein the rauwolfia alkaloid is reserpine, and trazodone, bupropion, and fluoxetine are administered, said reserpine, trazodone, bupropion and fluoxetine being administered in a regimen sufficient to supply effective daily dosages thereof for assisting weight loss.

10. The method of claim 1 wherein the rauwolfia alkaloid is reserpine, and both trazodone and bupropion are administered, said reserpine, trazodone, and bupropion being administered in a regimen sufficient to supply effective daily dosages thereof for assisting weight loss.

* * * * *